United States Patent [19]

Colley et al.

[11] 4,319,580

[45] Mar. 16, 1982

[54] METHOD FOR DETECTING AIR EMBOLI IN THE BLOOD IN AN INTRACORPOREAL BLOOD VESSEL

[75] Inventors: Peter S. Colley, Seattle; Roy W. Martin, Redmond, both of Wash.

[73] Assignee: The Board of Regents of the University of Washington, Seattle, Wash.

[21] Appl. No.: 70,356

[22] Filed: Aug. 28, 1979

[51] Int. Cl.³ .............................................. A61B 10/00
[52] U.S. Cl. .................................... 128/661; 128/696
[58] Field of Search ............................... 128/660–663, 128/349 R, 696; 73/19, 23–24, 861.41

[56] References Cited

U.S. PATENT DOCUMENTS

| | | | |
|---|---|---|---|
| 3,640,271 | 2/1972 | Horton | 128/662 |
| 3,921,622 | 11/1975 | Cole | 73/19 |
| 4,112,735 | 9/1978 | McKnight | 73/19 |
| 4,112,773 | 9/1978 | Abts | 73/19 |
| 4,122,713 | 10/1978 | Stasz et al. | 73/19 |

OTHER PUBLICATIONS

Fairbank, W. M. et al., "A New Non-Invasive Technique for Cardiac Pressure Measurement: Reson Scattering of UTS from Bubbles", IEEE BME Trans. vol. 24 No. 2, Mar. 1977, pp. 107–110.

Furness, A. et al., "Detection of Bubbles in Blood Vessels and Extra-Corporeal Circuits," Med. & Biol. Engrg. & Const. 1979, vol. 17, pp. 534–535.

*Primary Examiner*—Robert W. Michell
*Assistant Examiner*—Francis J. Jaworski

*Attorney, Agent, or Firm*—Christensen, O'Connor, Johnson & Kindness

[57] ABSTRACT

A system for detecting and quantifying air emboli in blood vessels which uses either an intravascular catheter 22 or an esophageal catheter 50. In a preferred embodiment, the intravascular catheter includes an elongated cylindrical tube of flexible material, the tube having a tip 22A and having formed therein an axial aspiration lumen 26 and a second axial lumen 28. An ultrasonic transducer 24, comprising an annular, cylindrical ring of piezoelectric material, is fitted over and secured to the tube adjacent its tip. A microcoaxial cable passes through lumen 28 and is electrically interconnected with the ultrasonic transducer. In a preferred embodiment, the esophageal catheter includes a substantially cylindrical member 54 on which is fitted an ultrasonic transducer 52 comprising an annular, cylindrical ring of piezoelectric material. An elongated tube 58 is secured to the substantially cylindrical member, and a microcoaxial cable 62 passes through tube 58 and the substantially cylindrical member and is electrically connected to the ultrasonic transducer. In use, the intravascular catheter is positioned within a desired blood vessel after percutaneous insertion, and the esophageal catheter is positioned within the esophagus below the bifurcation of the trachea. A pulsed Doppler circuit (FIG. 9) energizes the transducer and provides a Doppler signal from return signals generated by the transducer as a result of returns of transmitted ultrasonic energy. A circuit (FIGS. 10 and 11) processes the Doppler signal to obtain various information useful in the diagnosis of air emboli.

9 Claims, 11 Drawing Figures

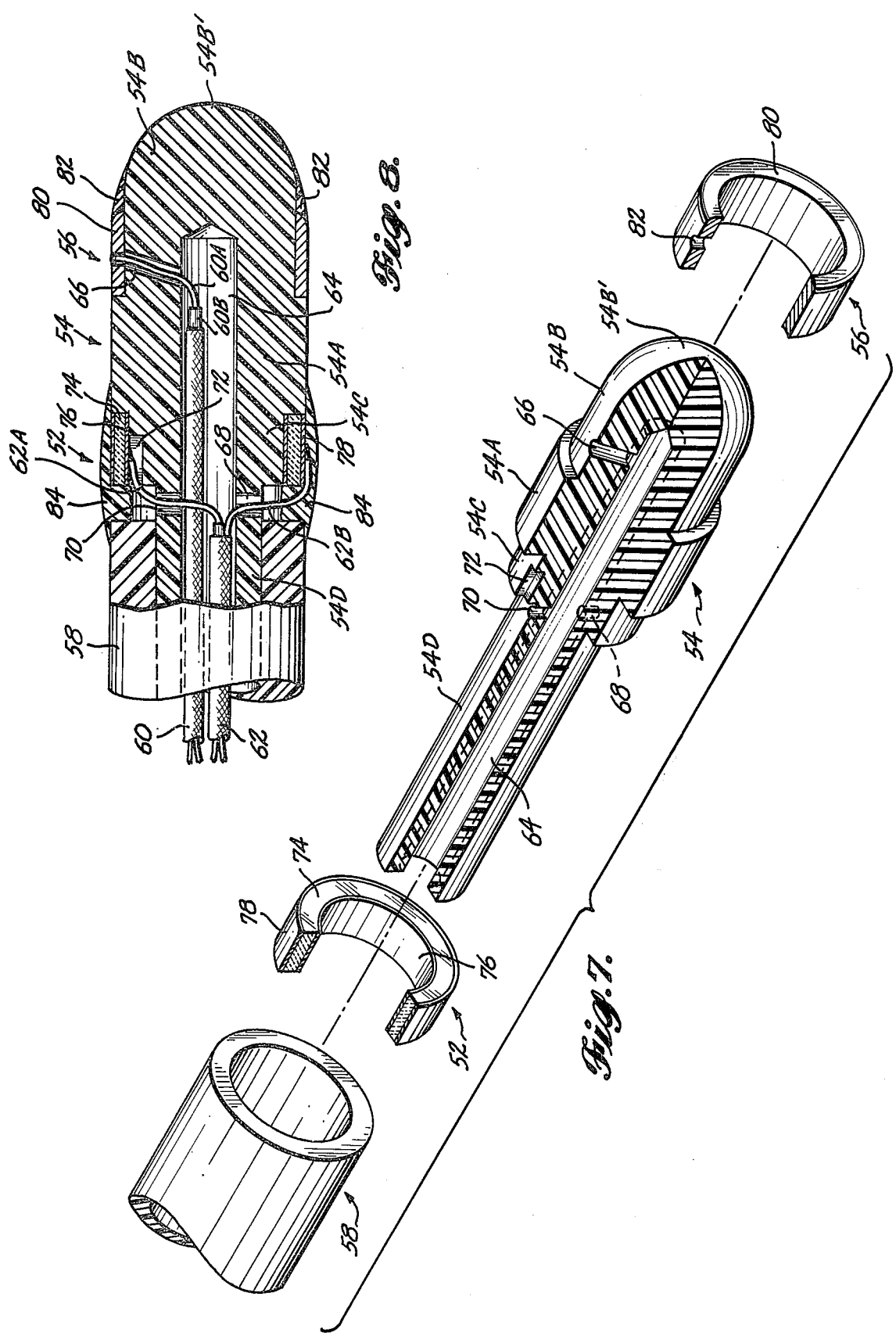

METHOD FOR DETECTING AIR EMBOLI IN THE BLOOD IN AN INTRACORPOREAL BLOOD VESSEL

This invention was made during the course of a grant from the Department of Health, Education and Welfare of the United States Government.

FIELD OF THE INVENTION

This invention generally relates to diagnostic methods and apparatus using ultrasonic energy, and, more particularly, to a method for detecting air emboli in the blood in an intracorporeal blood vessel through the use of ultrasonic energy.

BACKGROUND OF THE INVENTION

During various neurosurgical procedures on the head and neck, the patient is frequently placed in the sitting position in order to improve surgical exposure and drainage of blood away from the operative site. Despite its advantages, the sitting position introduces an unavoidable complication of air emboli, or intravascular air bubbles, as air enters open veins of the head and neck to be carried by the blood to the heart and lung. In sufficient amounts, air emboli can cause cardiac failure, hypotension, hypoxia and pulmonary edema.

It has been estimated that approximately 10,000 patients per year are exposed to the risk of air embolism as a result of undergoing neurosurgical operations while in the sitting position. The total incidence of air embolism in this position is about 20–30%. In cases where air embolism does occur, the incidence of severe embolism resulting in hypotension and hypoxia may be as high as 78%. In addition, it has been noted that there is a significant incidence of air embolism during any operation in which there is a major hydrostatic gradient between the operative site and the heart, i.e., the operative site is above the heart, whether the patient is in the sitting, supine, prone or lateral positions.

Treatment of air emboli may be effected: by aspirating, or withdrawing, the air through a catheter which has been pre-operatively introduced through a peripheral vein and advanced so that its tip is in the right atrium of the heart; by compression of the patient's jugular veins; by continuously flushing the wound with a saline solution; by detecting and blocking any open venous channels in the surgical wound; by application of 100% oxygen to the patient; or, by the administration of a vasopressor or an antiarrhythmic drug to the patient. These prophylactic methods are most effective when a diagnosis of air emboli is made at a time when only small amounts of air have entered the circulatory system.

The ability of the physician to make an early diagnosis of air emboli has been greatly facilitated by the use of an ultrasound instrument incorporating a precordial Doppler probe. Typically, such a probe includes a housing having a circular disk through which a transmitting tranducer and a receiving transducer located within the housing can respectively transmit and receive ultrasonic energy. The transducers are coupled with a circuit which applies a high frequency electrical signal (typically in the mHz range) to the transmitting transducer to cause the transmission of ultrasonic energy thereby in a fairly broad beam. Electrical output signals from the receiving transducer, resulting from returns of the transmitted ultrasonic energy from objects within the beam, are compared with the high-frequency electrical signal applied to the transmitting transducer to develop a Doppler signal representative of any frequency shift caused by relative movement between an object and the probe. The Doppler signal is then amplified and applied to a loudspeaker for audible reproduction.

In the use of the precordial Doppler probe, the disk of the probe is coated with a conductive jelly, and then placed on the patient's precordium and positioned until characteristic Doppler sounds produced by blood flow and vessel wall movement of the patient's heart are heard. Once the probe is positioned, the passage of even minute amounts of air through the patient's heart is accompanied by a characteristic Doppler sound that is higher in frequency and amplitude than the normal heart sounds, so diagnosis of air emboli can be made.

Although the use of ultrasound instruments incorporating a precordial Doppler probe has greatly improved the ability of the physician to diagnose air emboli, the technique suffers from several difficulties. Since the precise region of the patient's body being ensonified with ultrasonic energy is not known to the physician, the physician can not be sure that only a portion of the right side of the heart is being monitored. As a result, air emboli may pass through the right side of the heart without being detected. The problem of proper location of the transducer probe is intensified in obese patients and in heavy-breasted women, where returning ultrasonic energy is significantly attenuated by subcutaneous tissue.

Once the probe is positioned, it is then taped or strapped to the precordium. It is very difficult in many instances to secure the position of the probe on heavy-breasted women and obese patients, or when the patient is in the lateral or prone positions. Occasionally during pre-operative and operative procedures, the probe may be dislodged or may slip from position, especially when the patient is in the lateral or prone positions. A change of probe position may not be detectable, since characteristic heart Doppler sounds may continue to be produced, but may result in the loss of the physician's ability to detect the Doppler sounds characteristic of air emboli.

In addition to the aforementioned problems of properly positioning and securing the position of the precordial Doppler probe, which may result in the inability of the physician to diagnose air emboli, the use of a precordial Doppler probe is disadvantageous in that the Doppler sounds produced thereby which are characteristic of air emboli cannot be quantified, that is, there is no way for the physician to determine the amount of air that is passing into the right side of the heart over a given period of time. Because of difficulties in positioning the precordial Doppler probe, the ultrasonic beam therefrom is necessarily fairly broad so that air throughout the right side of the heart may be detected. Quite frequently, air emboli become entrapped in the right ventricle before passing on to the lungs. If an attempt is made to quantify the Doppler sounds that are characteristic of air emboli, the resultant determinination will include not only a component related to the amount of air entering the right side of the heart, but also a component related to the amount of air entrapped in the right ventricle. Therefore, since the physician is unable to determine how much air is entering the heart over a given period of time, he is likely to apply the various prophylactic methods discussed even in situations where such methods are not called for due to the small amount of air entering the venous system.

As previously discussed, one of these prophylactic methods is aspiration through an intravascular catheter. In order to be effective for aspiration, the tip of the catheter preferably should be located in the right atrium. The catheter tip is frequently located by X-ray equipment, or by using the catheter as an ECG lead and monitoring the patient's ECG for a P-wave change characteristic of the atrial position. These methods are time consuming, involve extra equipment, and typically are used only before an operation. There are many occasions when the catheter tip migrates away from the right atrium, either pre-operatively or operatively, when the patient is moved.

It is therefore an object of this invention to provide an improved method for the detection of air emboli in blood vessels.

It is a further object of this invention to provide such a method and apparatus which utilize ultrasonic energy.

It is another object of this invention to provide such a method which utilizes a catheter on which is located an ultrasonic transducer, which catheter is positioned within a body in proximity to a blood vessel.

It is yet another object of this invention to provide such a method which can be used to reliably position the catheter within the body by monitoring electrical signals from the transducer on the catheter.

It is still another object of this invention to provide a method which can be used to properly position an intravascular catheter in a blood vessel for aspiration of air emboli therefrom.

It is also an object of this invention to provide a method which provides for the early and reliable diagnosis of air emboli in blood vessels, notwithstanding the pre-operative or operative position of the patient or the patient's bodily characteristics.

SUMMARY OF THE INVENTION

Briefly, air emboli in the blood flow in an intracorporeal blood vessel are detected by the use of an elongated catheter on which is located, adjacent the tip of the catheter, an ultrasonic transducer means capable of ensonifying a substantially planar region. The catheter is positioned within a body containing the blood vessel so that the tip of the catheter is at least proximate to the blood vessel and so that the substantially planar region transects the blood vessel at a desired location therein. The ultrasonic transducer means is energized with a high frequency electrical signal so as to cause the ultrasonic transducer means to transmit ultrasonic energy in the substantially planar region. Electrical return signals generated by the ultrasonic transducer means, as a result of returns of the transmitted ultrasonic energy from objects in the substantially planar region, are detected and monitored for those return signals that are characteristic of air emboli.

The catheter may comprise either an intravascular catheter or an esophageal catheter. Either catheter may be reliably positioned by monitoring the electrical return signals from the ultrasonic transducer for those characteristic of blood flow at the desired location. If desired, the catheter may be provided with means adjacent the tip thereof for providing an ECG signal, and the catheter may be positioned by monitoring the ECG signal for the characteristics that the ECG signal will have when the tip of the catheter is at the desired location.

The method of the invention may be used to reliably position the tip of the intravascular catheter so as to allow the aspiration of air emboli from blood in the right side of the heart. The catheter tip is percutaneously inserted into the venous system of the body, and the ultrasonic transducer is caused to transmit ultrasonic energy. Return signals generated by the ultrasonic transducer as a result of returns of the transmitted energy are detected, and the catheter is advanced until the detected return signals are characteristic of blood flow into the right atrium of the heart.

BRIEF DESCRIPTION OF THE DRAWINGS

The invention can best be understood by reference to the following portion of the specification, taken in conjunction with the accompanying drawings in which:

FIG. 7 is a pictorial, exploded view showing the esophageal catheter;

FIG. 8 is a partial cross-sectional view of the esophageal catheter;

DESCRIPTION OF A PREFERRED EMBODIMENT

Before proceeding to a description of the invention, it is desirable to briefly review the circulatory system of the body, with particular emphasis on the mechanics of blood flow through the heart.

Figure 1:
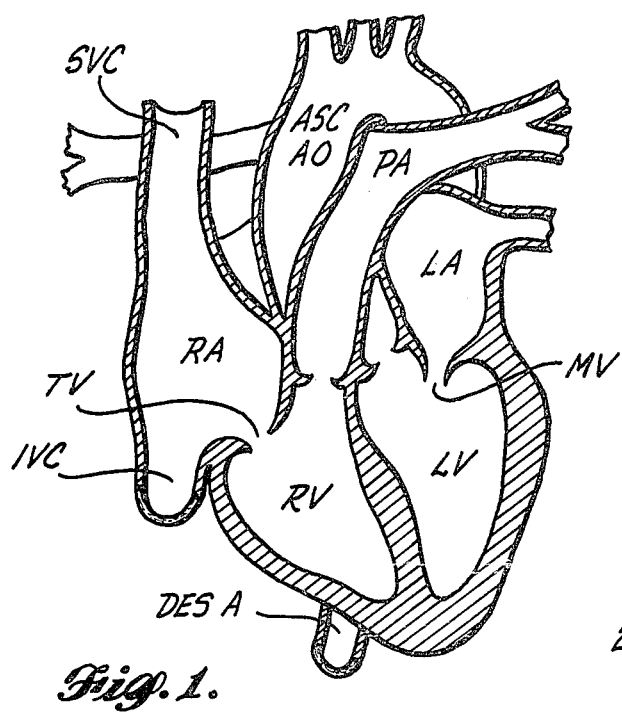
FIG. 1 is a cross-sectional view of a human heart.

With reference now to FIG. 1, deoxygenated blood collected by the venous system in the upper portion of the body is supplied to the superior vena cava (SVC) of the heart, and that from the lower part of the body is supplied to the inferior vena cava (IVC). Blood from the superior vena cava and the inferior vena cava flows into the right atrium (RA) of the heart, which in turn is coupled with the right ventricle (RV) of the heart by the one-way tricuspid valve (TV). Between each contraction of the right ventricle, blood is drawn from the right atrium through the tricuspid valve and then forced during contraction (through another one-way valve) to the pulmonary artery (PA), and thence to the lungs, where the blood is oxygenated. From the lungs, the oxygenated blood is supplied to the left atrium (LA) of the heart, which is coupled with the left ventricle (LV) by the one-way mitral valve (MV). Between each contraction of the left ventricle, the oxygenated blood is drawn from the left atrium through the mitral valve into the left ventricle, and then forced during contraction (through another one-way valve) to the ascending aorta (ASC AO) and the descending aorta (DES AO), and thence to the arterial system of the body.

The various physiological complications that arise from the presence of air emboli in the circulatory system occur when air emboli become entrapped in the right atrium, right ventricle, and pulmonary artery to accordingly block blood flow therethrough, so that detection and quantization of the amount of air emboli entering the right side of the heart over a given period of time is preferably made in the superior vena cava for air emboli resulting from surgical wounds in the venous system in the upper part of the body, and in the inferior vena cava for air emboli resulting from surgical wounds in the venous system in the lower part of the body. In addition, air may pass on rare occasions from the right side of the heart, e.g., the superior vena cava, the inferior vena cava, the right atrium, the tricuspid valve, and the right ventricle, through small openings in the septum divider to the left side of the heart and to the arterial system, so that it is accordingly desirable to diagnose air emboli in the right side of the heart.

Figure 2:
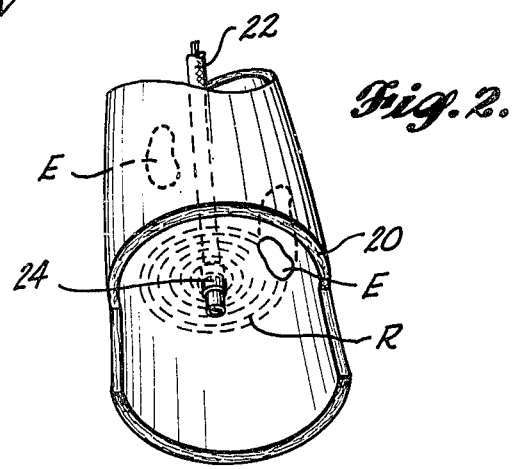
FIG. 2 is a cut-away view of a blood vessel, in particular, the portion of the right side of the heart just above the juncture of the superior vena cava and the right atrium, showing the positioning of an intravascular catheter therein in accordance with the method of the present invention.

With reference now to FIG. 2, the detection of air emboli in a blood vessel 20 carrying deoxygenated blood, such as the superior vena cava, is accomplished by the insertion of an intravascular catheter 22 therein. Located on catheter 22 is an ultrasonic transducer 24 which is particularly adapted to ensonify a substantially planar region R within blood vessel 20 with ultrasonic energy and to detect any returns of ultrasonic energy from objects within region R. Typically, ultrasonic energy will be returned from the blood cells and from air emboli E within blood vessel 20, and from the walls of blood vessel 20. As described in detail hereinafter, ultrasonic transducer 24 is provided with a high frequency electrical signal (the transmitted signal) which is converted by ultrasonic transducer 24 into ultrasonic energy. Returned ultrasonic energy is converted by ultrasonic transducer 24 into a corresponding electrical signal (the received signal) which is compared with the transmitted signal to develop a Doppler signal related to the frequency shift between the transmitted signal and the received signal occasioned by the movement of objects through region R. The Doppler signal is then processed in a particular manner to provide a filtered Doppler signal related only to the passage of air emboli E through region R, and is further processed, if desired, to develop a signal related to the amount of air emboli E passing through region R over a given period of time.

Figure 3:
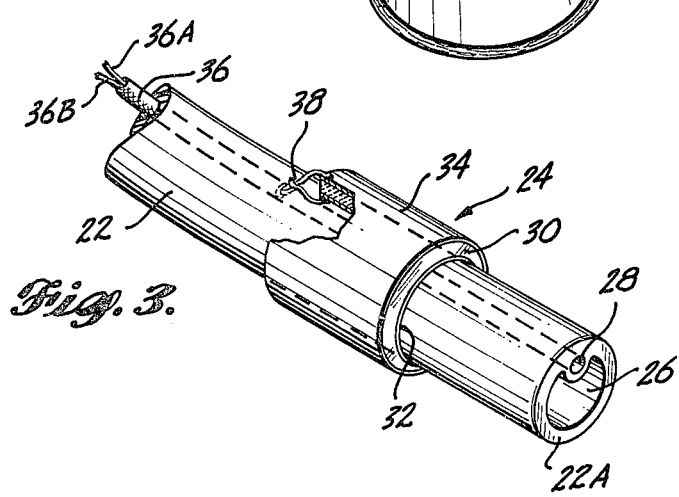
FIG. 3 is a pictorial, partially cut-away view showing the intravascular catheter.

A preferred form of the intravascular catheter 22 and ultrasonic transducer 24 is seen in FIG. 3. Catheter 22 is internally similar to the well-known Swan-Ganz catheter and comprises an elongated, cylindrical tube of flexible material which has formed therein longitudinally-extending, parallel passageways or lumens 26, 28. As illustrated, lumen 26 has a substantially greater cross-sectional area than does lumen 28. Transducer 24 comprises an annular, cylindrical ring 30 of piezoelectric material whose inner and outer cylindrical surfaces are provided with respective metallic, conducting layers 32, 34. A microcoaxial cable 36 having a central conductor 36A and a shield conductor 36B is inserted throughout the length of lumen 28 in catheter 22, and one end thereof is brought out through an aperture 38 formed in catheter 22 near its tip 22A and extending between lumen 28 and the exterior cylindrical surface of catheter 22. One of the conductors 36A, 36B is soldered to outer layer 34 and the other of the conductors 36A, 36B is soldered to inner layer 32. Transducer 24 is then slipped over the tip 22A of catheter 22 and slid therealong until transducer 24 is located a convenient distance from tip 22A.

Figure 4:
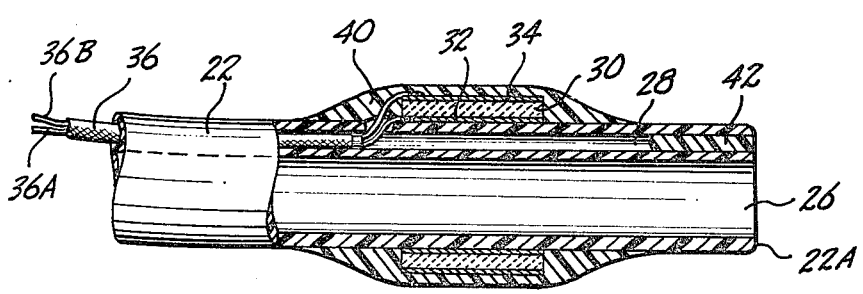
FIG. 4 is a partial cross-sectional view of the intravascular catheter.

With additional reference now to FIG. 4, transducer 24 is secured to catheter 22 by the application of a nonporous and electrically insulating material 40, such as an epoxy resin, over transducer 24 and the adjoining portions of the exterior cylindrical surface of catheter 22. Material 40 also serves to electrically insulate the layers 32, 34, the conductors 36A, 36B, and their soldered interconnections, from the fluid, e.g., blood, in which catheter 22 is inserted. Fluid entry into lumen 28 is also blocked by an appropriate sealing material 42 inserted into the end of lumen 28 adjacent tip 22A.

In use, a needle is inserted into an appropriate vein (for positioning the catheter 22 in or through the superior vena cava, either a vein in the elbow or an internal jugular vein is selected) and the catheter 22 is inserted through the needle and advanced along the vein. A detecting and quantifying apparatus, (e.g., FIGS. 9–10) is interconnected with the ends of conductors 36A, 36B protruding from the vein, and a high-frequency electrical signal is applied thereto to cause transducer 24 to emit ultrasonic energy as illustrated in FIG. 2. Returns of the ultrasonic energy from moving objects within region R cause ultrasonic transducer 24 to produce a corresponding output signal which is coupled via conductors 36A, 36B to the apparatus, and a Doppler signal is developed therefrom.

Preferably, transducer 24 is located on catheter 22 so that transducer 24 is positioned at the juncture of the superior vena cava (or inferior vena cava) and the right atrium when the tip 22A is positioned in the right atrium. By audibly reproducing the Doppler signal, the tip 22A of catheter 22 may be reliably positioned in the right atrium by advancing the catheter 22 until a change in Doppler sounds that is characteristic of the transition between the superior vena cava (or inferior vena cava) and the right atrium are heard. Proper positioning may also be facilitated by filling the lumen 26 of catheter 22 with a suitable conducting solution (e.g., a hypertonic saline solution), inserting an electrode into the portion of lumen 26 that exits from the vein, and connecting the electrode to an ECG monitor. In this case, proper positioning is detected upon display of the characteristic ECG waveform obtained from an electrode positioned in the right atrium.

As previously described, the passage of air emboli E through the region R of ensonification produces a Doppler sound which is higher in frequency and in amplitude than those characteristic of blood flow and vessel wall movement. Upon recognition of the Doppler sounds characteristic of air emboli, the physician may apply suction to lumen 26 to aspirate the air emboli, and may utilize the other prophylactic measures previously discussed.

In a working prototype of the invention, the catheter 22 was a No. 7 French double lumen catheter, and the transducer 24 had an inside diameter of 2.31 mm., an outside diameter of 3 mm., and a length of 3 mm. (Vernatron Model No. A-2-1015), and was operated at 4.7 mHz. The prototype, while providing acceptable operation, is too large to be inserted through a 14 gauge (1.8 mm. inside diameter) needle normally used for percutaneous puncture. It is preferred, therefore, that a smaller catheter and transducer be utilized. For example, a No. 6 French double lumen catheter, and a transducer having an inside diameter of 1.3 mm., an outside diameter of 1.6 mm., and a length of 1.63 mm. (Vernatron Model No. 1-1010), normally operable at 7 mHz, may be used. Preferably, the thickness of the transducer utilized should be as thin as possible, consistent with the frequency requirements for the detection of blood flow and air emboli (a frequency in the range of 0.5 to 30 mHz is believed to be acceptable) so as to allow the cross-sectional area of the lumen 26 to be as large as possible to permit effective aspiration of air emboli.

If the catheter 22 is left within the body for a considerable period of time, blood clots may form thereon which will significantly diminish the ability of the transducer 24 to transmit and receive ultrasonic energy. In such a case, it is preferable that the material 40 be modified by the addition of an anti-thrombotic agent, such as heparin, which has proven to be effective in preventing clotting over a substantial period of time. As an example, the anti-thrombotic agent may comprise F-68 heparin available from Wyandotte Chemical Corporation. In addition, the entire catheter 22 may be treated with heparin by rinsing the catheter in an appropriate solution containing heparin. The material 40 itself may comprise a relatively free-flowing, two-part liquid epoxy, such as Scotchcast No. 5, that can be applied to achieve a very thin coating over transducer 24 so as to not significantly attenuate transmitted and received ultrasonic energy.

There may be a reluctance on the part of the physician to utilize an intravascular catheter of the type previously described, particularly since the catheter includes a current-carrying conductor and is inserted into the blood stream with a consequent risk of inducing cardiac arrthymias if there is current leakage. For noninvasive detection and quantification of air emboli, an esophageal catheter may be utilized.

Figure 5:
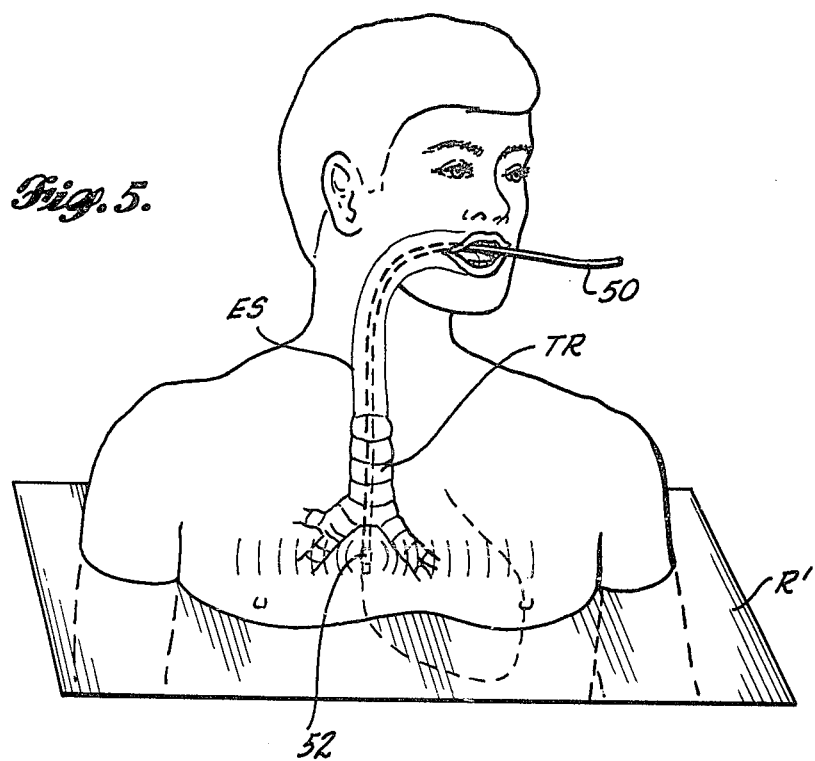
FIG. 5 is a pictorial view showing the insertion of an esophageal catheter into a patient in accordance with the method of the present invention.
Figure 6:
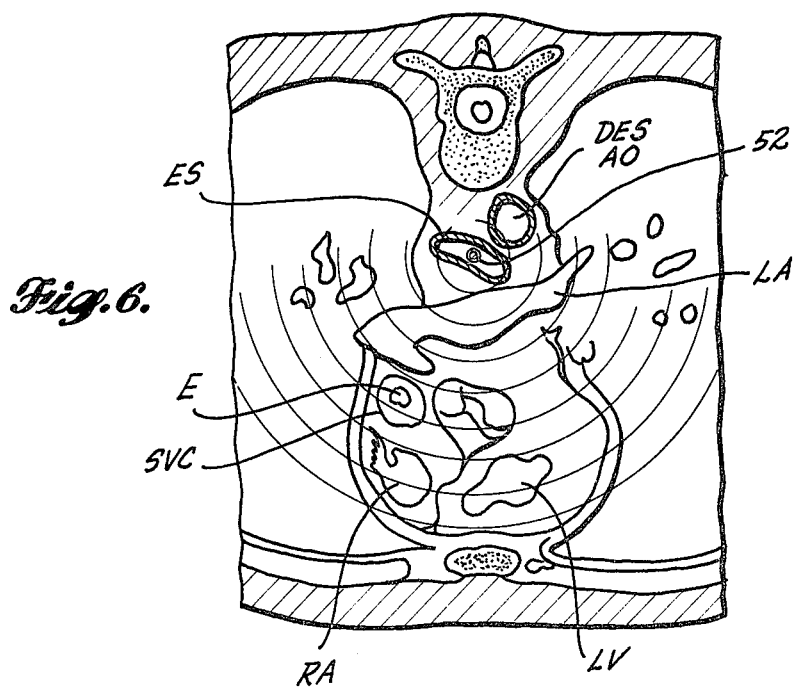
FIG. 6 is a cross-sectional view of the patient's internal organs in the region of the heart, showing the position of the tip of the esophageal catheter when inserted.

With reference now to FIG. 5, the esophageal catheter includes an elongated tube 50 on whose tip is located an ultrasonic transducer 52. Catheter 50 is inserted through the mouth of the patient and into the patient's esophagus (ES), and advanced until the tip of catheter 50 is just below the bifurcation of the patient's trachea (TR) which extends parallel to the esophagus. When the tip of catheter 50 is located below the bifurcation of the trachea, it will be in proximity to the heart as indicated by Doppler sounds characteristic of pulsatile blood flow. As also shown in FIG. 6, a substantially planar region R' of the patient's body including the heart will be ensonified, and ultrasonic energy returns from moving objects within region R' will be detectable by transducer 52. The region R' of ensonification includes the descending aorta (DES AO), the left atrium (LA), the superior vena cava (SVC), the right atrium (RA), the left ventricle (LV), and other objects. As described hereinafter with reference to FIGS. 9–10, the detecting and quantifying apparatus is made responsive only to returns of ultrasonic energy from objects lying within a predetermined range of radial distances from transducer 52. As an example, making the apparatus responsive only to returns from objects within a range of 6–10 cm. from transducer 52 will allow the detection of movement only through the superior vena cava, the right atrium, and the left ventricle, thereby allowing the detection of air emboli E in either the superior vena cava or the right atrium.

With reference now to FIGS. 7 and 8, the preferred form of the esophageal catheter 50 includes the ultrasonic transducer 52, a substantially cylindrical member 54, an ECG electrode 56, a length of flexible tubing 58, and a pair of microcoaxial cables 60,62.

Member 54, which is preferably fabricated from a plastic such as an acrylic, has a substantially cylindrical, central portion 54A, and a substantially cylindrical portion 54B projecting from one side of portion 54A and coaxial therewith, with portion 54B having a lesser diameter than that of 54A and with portion 54B terminating in a smooth, rounded tip 54B'. Projecting from the other side of portion 54A and coaxial therewith is a substantially cylindrical portion 54C whose diameter is also less than that of portion 54A. An elongated, substantially cylindrical portion 54D projects from portion 54C and is coaxial therewith, with portion 54D having a lesser diameter than that of 54C. A central bore 64 is formed in member 54 so as to extend from portion 54D, through portions 54C and 54A, to terminate in portion 54B, and radially-extending apertures 66, and 68, 70 are formed in member 54 so as to extend between bore 64 and the exterior, cylindrical surfaces of portions 54B and 54D, respectively. An axially-extending notch 72 is also formed in the exterior, cylindrical surface of portion 54C adjacent aperture 70.

Ultrasonic transducer 52 comprises an annular, cylindrical ring 74 of piezoelectric material having metallic, conducting layers 76, 78 formed on its inner and outer cylindrical surfaces, respectively. The diameter of portion 54C of member 54 is chosen to be substantially equal to the inside diameter of ring 74 and the diameter of portion 54A of member 54 is chosen to be substantially equal to the outside diameter of ring 74.

ECG electrode 56 also comprises an annular, cylindrical ring 80 of metallic, conducting material (such as silver) whose inside diameter is substantially equal to the diameter of portion 54B, and whose diameter is substantially equal to the diameter of portion 54A. A radial aperture 82 is provided in ring 80 and extends between the inner and outer cylindrical surfaces thereof.

Tubing 58 comprises an elongated length of surgical tubing, (e.g., Tygon), whose inner diameter is substantially equal to the diameter of portion 54D and whose outer diameter is substantially equal to the diameter of portion 54A. The length of tubing 58 may be varied so that the catheter can be used with different-sized patients, but a typical length is twenty inches.

In fabrication and assembly of the esophageal catheter, member 54 is formed by milling and drilling an appropriate length of an acrylic rod, or by molding an appropriate plastic material. After slipping the transducer 52 over portion 54D of member 54, the microcoaxial cables 60, 62 are inserted into bore 64. The center conductor 60A of cable 60 is terminated in aperture 82 in ring 80, and soldered thereto, and the shield conductor 60B thereof is left unconnected. Likewise, the center conductor 62A of cable 62 is brought out through aperture 70 and soldered to the inner layer 76 of transducer 52, and the shield conductor 62B thereof is brought out through aperture 68 and soldered to the outer layer 78. Thereafter, ECG electrode 56 is slipped onto portion 54B and transducer 52 is slipped onto portion 54C, with a portion of conductor 62A being received in notch 72.

To complete the catheter, the portions of cables 60, 62 protruding from portion 54D are routed through tubing 58, portion 54D is inserted into tubing 58, and tubing 58 advanced to a position adjacent to portion 54C. If desirable, the exterior, cylindrical surface of portion 54D may be coated with an adhesive or may be provided with ribs to assist in retention of tubing 58 on portion 54D. A sealing material 82, such as an epoxy resin (Scotchcast No. 5), is applied to the forward end of ring 80 and the adjoining part of portion 54B to provide a smooth transition to tip 54B', and a similar material 84 is applied over transducer 52 and the junctures of transducer 52 with portion 54A and tubing 58 to provide an electrical and fluid seal.

As an example, the outside diameter of the transducer 52, and therefore the diameter of portion 54A of member 54, and the outside diameters of ring 80 and tubing 58, may be 6.35 mm.; the inside diameter of transducer 52, and therefore the diameter of portion 54C, may be 5 mm.; the length of transducer 52, and therefore the length of portion 54C, may be 2.16 mm.; the length of ring 80, may be 2.54 mm.; the inside diameter of ring 80, and therefore the diameter of portion 54B, may be 5.6 mm.; the length of portion 54A may be 3.8 mm.; the length of portion 54D may be 13.1 mm.; the diameter of portion 54D may be 3.3 mm.; and, the inside diameter of tubing 58 may be 3.18 mm.

In the preferred form of the intravascular and esophageal catheters, the transducers 24, 52 thereof comprise annular, cylindrical rings of piezoelectric material, a configuration that is desirable to obtain omnidirectional transmission and reception of ultrasonic energy in a substantially planar region of ensonification. In addition, only a single transducer is used for both the transmission and reception of ultrasonic energy in order to meet the size constraints imposed upon the intravascular and esophageal catheters and in order to simplify the detecting and quantifying apparatus to be described. However, it is certainly feasible to configure the transducers in another manner, e.g., to use separate transducers on each catheter for transmission and reception of ultrasonic energy. Or, a plurality of transmit/receive crystals may be mounted in an array around the periphery of a cylindrical catheter, with the crystals being connected in parallel to form a single transducer, with each crystal being adapted to transmit and receive ultrasonic energy within a predetermined sector, and with the respective sectors of the crystals overlapping at a distance from the cylindrical surface of the catheter which is sufficient to allow the detection of air emboli. It is also feasible to use a single transducer having a sector-like beam and to mechanically rotate the transducer so as to scan the desired ensonification region, or to use an array of such transducers which are electrically scanned through the desired ensonification region. In all cases, it is preferable that the height of the transducer beam, in a direction parallel to the axial direction of the associated catheter, be as small as possible so that only a substantially planar region is ensonified.

It is also contemplated that sensors in addition to an ultrasonic transducer can be mounted on either the intravascular or the esophageal catheters. As an example, the esophageal catheter 50 illustrated in FIGS. 7 and 8 includes the ECG electrode 56 which allows the monitoring of the patient's ECG waveform. A similar ECG electrode may be located on the intravascular catheter 22 (in place of filling the lumen 26 with an electrically-conductive solution). Other types of sensors, such as pressure transducers, temperature sensors, and the like, may also be conveniently located on each catheter near the tip thereof, and interconnected with appropriate apparatus by cables passing through the catheter.

It will be recognized that the intravascular and esophageal catheters afford significant advantages in use over the precordial Doppler probe. Both catheters can be easily and reliably positioned so as to ensonify the right side of the heart, and the quality of the return signals obtained therefrom is unaffected by bodily characteristics such as the amount of breast or chest tissue of the patient. The position of the catheters can be continuously monitored during surgical procedures (by listening to the Doppler sounds produced thereby) to insure that the tips thereof have not shifted in position. In addition, because the intravascular catheter's position can be continuously monitored, the physician can be assured that the catheter will be properly positioned for the aspiration of air emboli if needed. Finally, because the ensonification region of the catheter can be reliably determined, it is possible to use the Doppler signal therefrom to quantify the amount of air emboli passing through a blood vessel over a predetermined period of time.

Figure 9:
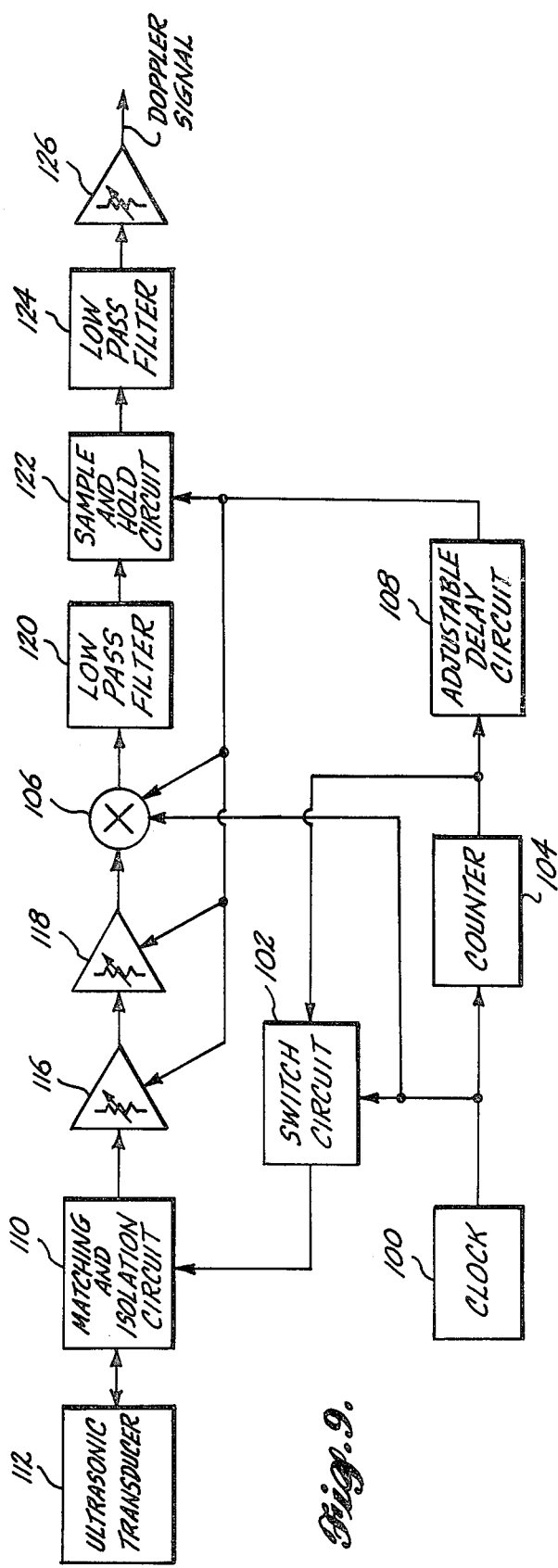
FIG. 9 is a block diagram of a first portion of a detecting and quantifying apparatus that is particularly adapted to provide a Doppler signal by the use of an ultrasonic transducer located on either the intravascular or the esophageal catheter.

Referring now to FIG. 9, the detecting and quantifying apparatus includes a clock 100, such as a crystal-stabilized oscillator, that provides an output signal including a train of pulses whose frequency is matched to the ultrasonic transducer being utilized (for the preferred form of the intravascular and esophageal catheters previously described, respective frequencies of 7 and 4 mHz). The output signal from clock 100 is applied to a switch 102, a counter 104, and to one input of a mixer 106. Counter 104 is operative to divide the frequency of the pulses in the output signal from clock 100 by a fixed integer. Therefore, the output signal from counter 104 comprises a series of pulses whose frequency is an integral submultiple of the frequency of the pulses in the output signal from clock 100. As an example, where the frequency of the output signal from clock 100 is 4 mHz, counter 104 may provide a pulse for every 512 input pulses thereto, whereby the frequency of the output signal from counter 104 is 36 kHz.

The output signal from counter 104 is applied to switch circuit 102, and to an adjustable delay circuit 108. Normally, switch circuit 102 is opened. However, in response to each pulse applied thereto from counter 104, switch circuit 102 closes for a predetermined period of time to accordingly couple the output signal from clock 100 to the output of switch circuit 102. Switch circuit 102 may be also designed so that power amplification occurs with respect to the power of the output signal from clock 100.

The output of switch circuit 102 is coupled to a matching and isolation circuit 110 which in turn is coupled with the ultrasonic transducer 112 by a suitable coaxial connector and the microcoaxial cable of the catheter, and also with the input of a preamplifier 116. Matching and isolation circuit 110 functions to match the output impedance of switch 102 and the input impedance of preamplifier 116 with that of ultrasonic transducer 112, to permit effective signal transfer, and also functions to protect preamplifier 116 from the relatively high-amplitude pulses present on the output of switch circuit 102. Accordingly, when switch circuit 102 is closed by counter 104, the output signal from clock 100 is applied to the ultrasonic transducer 112 for a short period of time, whereby ultrasonic transducer 112 emits a short burst of ultrasonic energy. Any returns of ultrasonic energy from objects within the ensonification region, that occur after switch circuit 102 is again opened and the output signal from clock 100 is removed from ultrasonic transducer 112, are converted by ultrasonic transducer 112 into a corresponding, low amplitude output signal which is coupled through matching and isolation circuit 110 to the iput of preamplifier 116. The duration of the burst of ultrasonic energy from ultrasonic transducer 112 should be long enough so that sufficient ultrasonic energy is supplied to all objects within the ensonification region, but should be short enough so that returns of ultrasonic energy from objects near the transducer are not masked by the energy still being emitted. As an example, the predetermined period of time during which switch 102 is closed may be such as to couple six cycles of the output signal from clock 100 to matching and isolation circuit 110.

The output of preamplifier 116 is connected to the input of a logarithmic amplifier 118 whose output is connected to another input of mixer 106. The output of mixer 106 is coupled through a first low-pass filter 120 to the input of a sample and hold circuit 122, and the output of sample and hold circuit 122 is coupled through a second low-pass filter 124 to the input of an adjustable-gain amplifier 126.

The output of adjustable delay circuit 108 is coupled to respective enabling inputs of preamplifier 116, logarithmic amplifier 118, mixer 106, and sample and hold circuit 122. Adjustable delay circuit 18 functions to provide an output pulse for each pulse applied thereto from counter 104, with each output pulse from adjustable delay circuit 108 beginning at a first, predetermined time from the time of occurrence of each pulse from counter 104 and terminating at a second, predetermined time, the first and second predetermined times being adjustable. Preamplifier 116, logarithmic amplifier 118 and mixer 106 are disabled, and sample and hold circuit 122 is in a hold state, during the absence of an output pulse from adjustable delay circuit 108. Conversely, preamplifier 116, logarithmic amplifier 118 and mixer 106 are enabled, and sample and hold circuit 122 is in a sample state, during the presence of an output pulse from adjustable delay circuit 108.

To describe the operation of the portion of the detecting and quantifying apparatus illustrated in FIG. 9, let it be assumed that the ultrasonic transducer 112 is located on the esophageal catheter (e.g., transducer 52 on catheter 50), and that the esophageal catheter has been properly positioned within the esophagus as previously described. In response to each output pulse from counter 104, the ultrasonic transducer is caused to emit a short burst of ultrasonic energy. After termination of this burst, electrical return signals representing returns of ultrasonic energy from objects within the region of ensonification are coupled to the input of preamplifier 116. Since the time required for ultrasonic energy to travel to and from an object is directly proportional to the distance between the transducer and the object, it will be seen that any return signal from the ultrasonic transducer representing returned ultrasonic energy from a given object will be delayed from the time of occurrence of the output pulse from counter 104 by an amount proportional to the distance between the object and the transducer. By appropriate adjustment of the time interval during which an output pulse is provided by adjustable delay circuit 108, only those return signals representing returns from objects within an area of interest within the ensonification region may be detected. With reference again to FIG. 6, the area of interest may be selected to include the superior vena cava and the right atrium, e.g., an annular area of 6-10 cm. from the ultrasonic transducer 52. Therefore, return signals from other objects that might tend to mask returns from blood flow and air emboli within the superior vena cava and the right atrium, e.g., returns from blood flow within the descending aorta (DES AO) and the left atrium (LA), are blocked.

The return signals are preamplified to a usable level in preamplifier 116, and are further passed through logarthmic amplifier 118 which provides for the selective compression of the amplitude range of the return signals. To aid in positioning the catheter, the amplitude compression of the return signals is selected so that low-amplitude return signals are amplified more than relatively-high amplitude return signals. For quantification of air emboli, however, it is preferable that no amplitude compression be provided and thus logarthmic amplifier 118 may be caused to operate as a linear amplifier. The return signals are mixed in mixer 106 with the output signal from clock 100, whereby the output signal from mixer 106 contains both sum and difference frequencies of the return signals and of the output signal from clock 100. The sum frequencies, being of no interest, are eliminated in low-pass filter 120 (whose cut-off frequency may be 1 mHz). The difference frequencies, or, the Doppler frequencies resulting from relative movement between objects within the area of interest and the ultrasonic transducer, are passed through sample and hold circuit 122, further filtered in low-pass filter 124 to remove high frequency noise, and amplified in amplifier 126 to provide an output Doppler signal. Typically, the Doppler frequencies of interest, including those from blood flow, vessel wall, and air emboli, are in the range of 0-3 kHz, whereby low-pass filter 124 may have a cutoff frequency of 3 kHz.

When the circuit of FIG. 9 is utilized with the intravascular catheter, it is not necessary to inhibit the detection of return signals from objects closely proximate the transducer, inasmuch as the transducer (and the catheter) are located within the blood vessel. Accordingly, adjustable delay circuit 108 may cause the production of an output pulse therefrom immediately upon the application of a pulse from counter 104 thereto (e.g., the first predetermined time may be adjusted to zero). Alternatively, adjustable delay circuit 108 and sample and hold circuit 122 can be eliminated, with low-pass filter 120 being interconnected directly with low-pass filter 124, and preamplifier 116, logarthmic amplifier 118, and mixer 106 being maintained in an enabled state at all times.

Those skilled in the art will recognize the circuit in FIG. 9 as similar to a conventional pulsed Doppler. The circuit is distinguished therefrom, however, in that the "range gate" used for the esophageal catheter (e.g., that provided by the output pulse from adjustable delay circuit 108) has a relatively longer duration than those normally used, and in that no such "range gate" is used for the intravascular catheter. Such a pulsed Doppler circuit allows a single ultrasonic transducer to be used for both the transmission and reception of ultrasonic energy. However, by appropriate design of the matching and isolation circuit 110, a continuous wave (CW) Doppler circuit can also be used with a single ultrasonic transducer, particularly in the case of the intravascular catheter. A CW Doppler circuit may also be used with the esophageal catheter, provided that the ultrasonic transducer is capable of transmitting and receiving ultrasonic energy in a predetermined, directional sector which can be mechanically or electrically oriented to the location of the superior vena cava and the right atrium (reference FIG. 6) so as to inhibit any returns from other objects such as the descending aorta.

Figure 10:
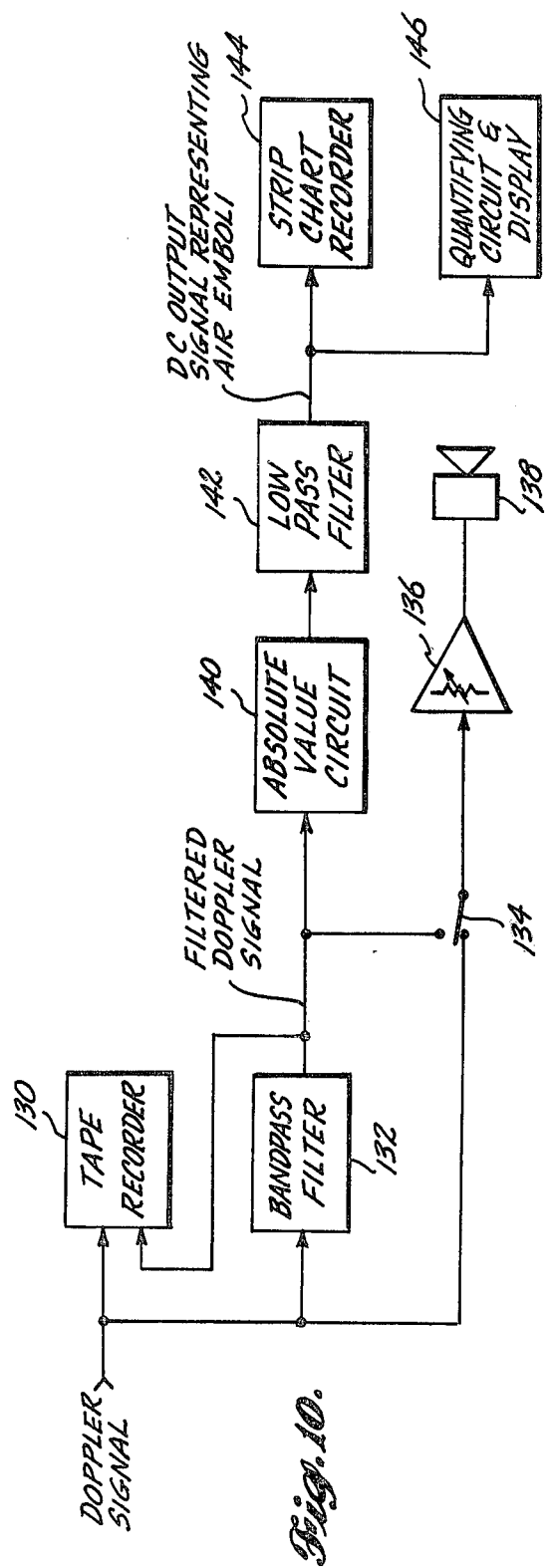
FIG. 10 is a block diagram of a second portion of the detecting and quantifying apparatus that is particularly adapted for recording, audibly reproducing, quantifying and displaying information relating to air emboli obtained from the Doppler signal; and, FIG. 11 is a block diagram of a quantifying circuit and display in FIG. 10.

The Doppler signal on the output of amplifier 126 accordingly contains Doppler frequencies representative of blood flow, vessel wall movement, and air emboli, if any, within the ensonified region, and is preferably applied to the portion of the detecting and quantifying apparatus in FIG. 10.

In particular, the Doppler signal is applied to the input of a tape recorder 130 and to the input of a bandpass filter 132. As previously discussed, air emboli passing through the ensonified region will result in the production of Doppler frequencies that are higher than those normally produced as a result of blood flow and vessel wall movement. The passband of bandpass filter 132 is accordingly chosen to be equal to the expected range of frequencies in the Doppler signal resulting from air emboli, e.g., 1–2 kHz. Present on the output of bandpass filter 132 is accordingly a filtered Doppler signal, representative only of air emboli, that is applied to another input of tape recorder 130. Preferably, tape recorder 130 comprises a multi-track tape recorder which provides for the simultaneous recording of both the Doppler signal and the filtered Doppler signal, thereby allowing subsequent off-line playback and analysis. The filtered Doppler signal and the Doppler signal are respectively applied to first and second stationary contacts of a switch 134 whose movable contact is connected to the input of an adjustable-gain, audio amplifier 136. A loudspeaker 138 connected to the output of amplifier 136 provides for the audible reproduction of either the Doppler signal or the filtered Doppler signal, depending on the position of switch 134. Therefore, the Doppler sounds characteristic of blood flow and vessel wall movement may be reproduced to position and to check the position of the catheter, or only the Doppler sounds characteristic of air emboli may be reproduced to aid in the diagnosis of air emboli.

The filtered Doppler signal is also applied to the input of an absolute value circuit 140 whose output is coupled through a low-pass filter 142 to the respective inputs of a strip chart recorder 144 and a quantifying circuit and display 146. Absolute value circuit 140 and low-pass filter 142 function as a full-wave rectifier and filter circuit to accordingly provide a DC output signal whose amplitude is proportional to the amplitude envelope of the filtered Doppler signal.

The amplitude envelope of the filtered Doppler signal, and therefore the amplitude of the DC output signal from low-pass filter 142, is proportional to the area of air emboli passing through the ensonified region at any given point in time. By recording the DC output signal from low-pass filter 142 on a continuously moving strip of paper by the use of strip chart recorder 144, the physician may be apprised of changes in the flow rate of air emboli through the ensonified region. In order to obtain information as to the amount of air emboli entering the right side of the heart, however, further signal processing, such as that provided by the embodiment of the quantifying circuit and display 146 illustrated in FIG. 11, is required.

The DC output signal representing air emboli (from low-pass filter 142) is applied, through a resistor 150, to the inverting input of an operational amplifier 152, and directly to the non-inverting input of a comparator 154. The inverting input of comparator 154 is supplied with a reference signal whose DC level is adjustable by the selective positioning of a potentiometer 156 connected between a source of supply potential $V_s$ and ground potential. A capacitor 158 and a semiconductor switch 160, schematically illustrated in FIG. 11, are connected in shunt between the input and the output of operational amplifier 152, whereby operational amplifier 152, resistor 150 and capacitor 158 function as an integrator which is resettable by closure of switch 160. The output of operational amplifier 152 is coupled to the inverting input of a second comparator 162 whose non-inverting input is supplied with a reference signal whose DC level is adjustable by the selective positioning of a potentiometer 164 connected between the supply potential $V_s$ and ground potential.

The output of comparator 162 is coupled to the input of a monostable multivibrator 166 whose Q output is coupled to the input of a counter 168 and whose Q output is coupled to a first input of an OR gate 170. The output of comparator 154 is connected to a second input of OR gate 170. The output of counter 168 is applied in parallel to an alarm circuit 172, a digital display 174, and a numerical printer 176. A clock 178 provides appropriate timing signals to counter 168, numerical printer 176, and to a third input of OR gate 170 through an inverter 180. The output of OR gate 170 is coupled to the control input of semiconductor switch 160.

Figure 11:
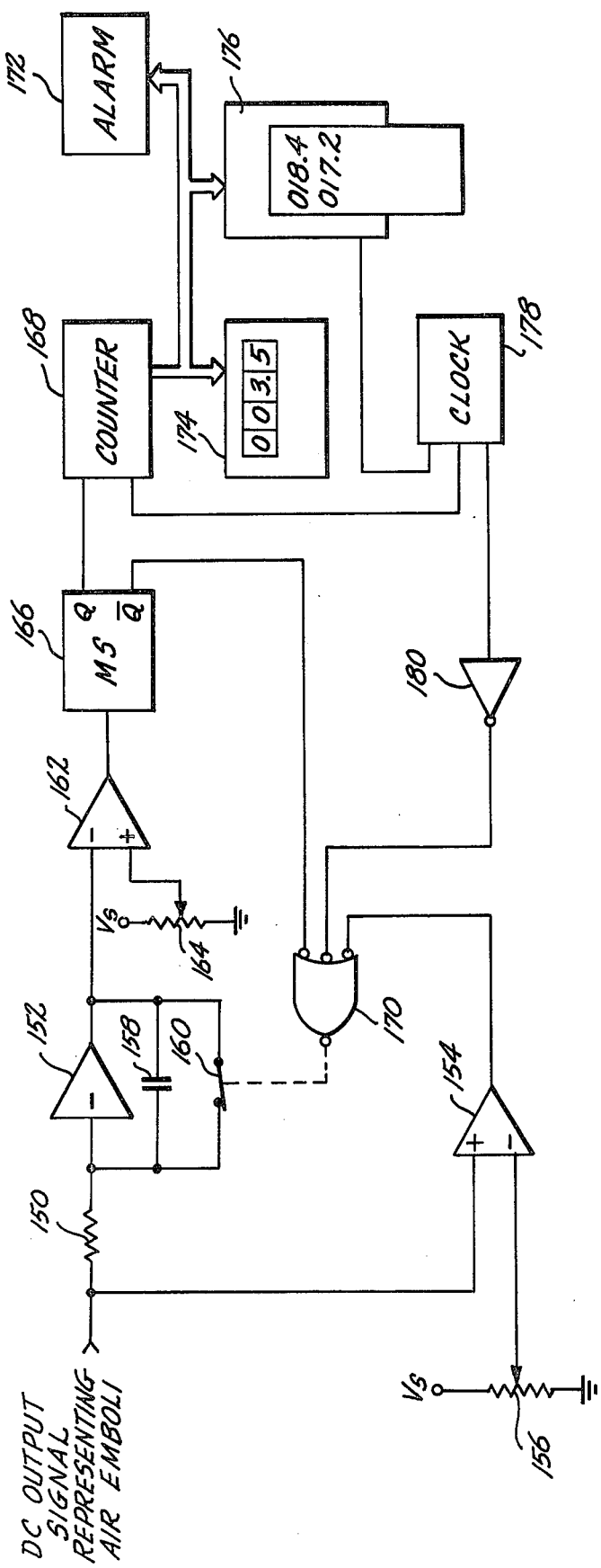

In operation of the quantifying circuit and display in FIG. 11, the DC level of the reference signal supplied to comparator 154 is adjusted so that comparator 154 provides a positive output signal only for amplitudes in the DC output signal representing air emboli that exceed the normal baseline variation in the DC output signal. During the absence of air emboli, a negative output signal from comparator 154 will cause OR gate 170 to maintain semiconductor switch 160 closed, so that the integrator including operational amplifier 152 is reset. Upon the presence of air emboli, however, a positive output signal from comparator 154 causes OR gate 170 to open switch 160.

When switch 160 is opened, the output signal from operational amplifier 152 begins to decrease at a rate determined by the amplitude of the integrator input signal and an integration period established by the values of resistor 150 and capacitor 158. By appropriate choice of the DC level of the reference signal supplied to comparator 162, comparator 162 will provide an output signal upon the passage of a predetermined volume of air, e.g., 0.1 ml., through the ensonified region. In response to each output signal from comparator 162, monostable multivibrator 162 will develop an appropriate pulse therefrom which will increment counter 168, and which will also, through OR gate 170, reset the integrator by momentary closure of switch 160 to allow further integration to proceed.

The timing signal supplied by clock 178 to counter 168 is preferably provided at predetermined intervals, e.g., 15 minutes, so that counter 168 accordingly contains a real-time count of the amount of air emboli passing through the ensonified region during each such time period. This count is directly displayed by means of digital display 174 continuously during each time period, and the count at the end of each time period is recorded and printed by numerical printer 176 under control of an appropriate timing signal from clock 178. Further, alarm circuit 172 is adapted to compare the count within counter 168 with a predetermined count representing a danger level of air emboli, and to provide an audible or visual alarm indication if the predetermined count is exceeded. To insure that normal drift in the integrator does not result in an output signal therefrom whose DC level exceeds that of the reference signal, switch 160 is also closed at periodic intervals, e.g., every 30 seconds, to reset the integrator by the timing signal supplied by clock 178 through inverter 180 and OR gate 170.

Therefore, by the use of that portion of the detecting and quantifying apparatus illustrated in FIGS. 10 and 11, the physician may hear the Doppler sounds characteristic of the heart or of air emboli alone, be provided with a strip chart recording of the amplitude of the Doppler sounds characteristic of air emboli, be provided with an alarm upon the detection of a dangerous quantity of air emboli, obtain a visual display of the quantity of air emboli at any time during a predetermined time period, and obtain a print out of the quanity of air emboli during each such predetermined time period. In addition, the strip chart recording, the print out, and a tape recording including both filtered and unfiltered Doppler sounds are made available for later study.

While the invention has been described with reference to a preferred embodiment, it is to be clearly understood by those skilled in the art that the invention is not limited thereto. In addition to the numerous examples of equivalents already given, it should be also noted that it is not required to use pulsed Doppler and CW Doppler circuits in carrying out the method of the present invention. While the phenomenon of differential returns of ultrasonic energy from air emboli, on the one hand, and from blood, on the other hand, is not fully understood, it is known that this phenomenon is due in part to the greatly-differing acoustic transmission capacities of air and blood. Therefore, any ultrasound detecting method and apparatus which can effectively respond to these differing acoustic transmission capacities may be utilized. Accordingly, the scope of the invention is to be determined only in accordance with the appended claims.

The embodiments of the invention in which an exclusive property or privilege is claimed are defined as follows:

1. A method for detecting air emboli in the blood in an intracorporeal blood vessel, by the use of an elongated catheter on which is located, adjacent a tip of said catheter, an ultrasonic transducer means capable of ensonifying a substantially planar region that extends radially outwardly from said transducer means and which is oriented transversely with respect to the longitudinal axis of said elongated catheter, said method comprising the steps of:
   (a) positioning said catheter within a body containing said blood vessel so that said tip of said catheter is at least proximate to said blood vessel and so that said substantially planar region transects said blood vessel at a desired location therein;
   (b) energizing said ultrasonic transducer means with a high frequency electrical signal so as to cause said ultrasonic transducer means to transmit ultrasonic energy radially outwardly in said substantially planar region;
   (c) detecting electrical return signals generated by said ultrasonic transducer means as a result of returns of said transmitted ultrasonic energy from objects in said substantially planar region; and
   (d) monitoring said detected electrical return signals for those characteristic of air emboli.

2. A method as recited in claim 1, wherein said catheter is positioned by monitoring said detected electrical return signals for those characteristic of blood flow at said desired location in said blood vessel.

3. A method as recited in claim 1, for use with a catheter which includes means adjacent said tip thereof for providing an ECG signal, wherein said catheter is positioned by monitoring said ECG signal for the characteristics that said ECG signal has when said catheter tip is at said desired location in said blood vessel.

4. A method as recited in claim 1, for use with an intravascular catheter, wherein said intravascular catheter is positioned within said blood vessel after percutaneous insertion and advancement of said catheter tip to said desired location in said blood vessel.

5. A method as recited in claim 4, wherein said blood vessel comprises the right side of the heart, and wherein said intravascular catheter is positioned by percutaneous insertion of said catheter tip into the venous system and advancement of said catheter tip until said catheter tip is located within the right atrium of the heart.

6. A method as recited in claim 5, wherein said intravascular catheter is reliably positioned by advancing said catheter tip until said detected electrical return signals are characteristic of blood flow into the right atrium.

7. A method as recited in claim 1, for use with an esophageal catheter, wherein said esophageal catheter is positioned in proximity to said blood vessel after insertion of said catheter tip into and advancement of said catheter tip along the esophagus.

8. A method as recited in claim 7, wherein said esophageal catheter is reliably positioned by advancing said catheter tip along the esophagus until said catheter tip is inferior to the bifurcation of the trachea and said detected electrical return signals are characteristic of pulsatile blood flow.

9. A method for reliably positioning the tip of an intravascular catheter so as to allow the aspiration of air emboli from blood in the right side of the heart, said method comprising the steps of:
   (a) locating an ultrasonic transducer means on said intravascular catheter adjacent the tip thereof;
   (b) percutaneously inserting said catheter tip into the venous system of the body;
   (c) causing said ultrasonic transducer means to transmit ultrasonic energy, and detecting return signals, generated by said ultrasonic transducer means as a result of returns of said transmitted ultrasonic energy;
   (d) advancing said catheter until said detected return signals are characteristic of blood flow into the right atrium of the heart.

* * * * *